United States Patent
Oren

(10) Patent No.: US 10,107,483 B2
(45) Date of Patent: Oct. 23, 2018

(54) HEADLIGHT

(71) Applicant: Kerr Corporation, Orange, CA (US)

(72) Inventor: Matthew Christopher Oren, Middleton, WI (US)

(73) Assignee: Kerr Corporation, Orange, CA (US)

(*) Notice: Subject to any disclaimer, the term of this patent is extended or adjusted under 35 U.S.C. 154(b) by 0 days.

(21) Appl. No.: 15/362,925

(22) Filed: Nov. 29, 2016

(65) Prior Publication Data

US 2017/0159917 A1 Jun. 8, 2017

Related U.S. Application Data

(60) Provisional application No. 62/263,310, filed on Dec. 4, 2015.

(51) Int. Cl.
| | |
|---|---|
| A61B 90/35 | (2016.01) |
| A61C 1/08 | (2006.01) |
| F21V 15/01 | (2006.01) |
| F21V 21/084 | (2006.01) |
| F21V 5/00 | (2018.01) |
| A61B 90/50 | (2016.01) |
| F21W 131/20 | (2006.01) |
| F21Y 115/10 | (2016.01) |

(52) U.S. Cl.
CPC ............ *F21V 21/084* (2013.01); *A61B 90/35* (2016.02); *A61C 1/088* (2013.01); *F21V 5/008* (2013.01); *F21V 15/01* (2013.01); *A61B 2090/502* (2016.02); *F21W 2131/20* (2013.01); *F21Y 2115/10* (2016.08)

(58) Field of Classification Search
CPC ........ F21V 21/084; F21V 5/008; F21V 5/048; A61C 1/088; A61B 90/35; A61B 2090/502
See application file for complete search history.

(56) References Cited

U.S. PATENT DOCUMENTS

| | | |
|---|---|---|
| 3,745,993 A | 7/1973 | Feinbloom |
| 4,104,709 A | 8/1978 | Kloots |
| 5,035,961 A | 7/1991 | Riley |
| 5,042,048 A | 8/1991 | Meyer |
| 5,331,357 A | 7/1994 | Cooley et al. |
| 5,774,271 A * | 6/1998 | Lagerway ............... F21L 14/00 359/649 |
| 5,924,234 A | 7/1999 | Bindon et al. |
| 6,290,368 B1 | 9/2001 | Lehrer |
| 7,261,438 B2 | 8/2007 | Alessio |
| 7,314,300 B1 | 1/2008 | Dorr et al. |

(Continued)

OTHER PUBLICATIONS

European Patent Office, Extended Search Report issued in corresponding European Application No. 16201896.4, dated Jan. 19, 2017.

(Continued)

*Primary Examiner* — Alexander Garlen
(74) *Attorney, Agent, or Firm* — Wood Herron & Evans LLP

(57) ABSTRACT

A headlight of the type worn by medical and dental professionals includes a housing having an opening therein. A light source is positioned in the housing to output light through the opening. A singlet lens is mounted in the housing proximate the opening, and a doublet lens is disposed between the light source and the singlet lens.

23 Claims, 2 Drawing Sheets

(56) References Cited

U.S. PATENT DOCUMENTS

| | | |
|---|---|---|
| 7,465,078 B2 | 12/2008 | Chang |
| 7,513,660 B2 | 4/2009 | Spartano et al. |
| D601,975 S | 10/2009 | Chang |
| D602,185 S | 10/2009 | Chang |
| 7,625,101 B2 | 12/2009 | Alessio |
| 7,626,705 B2 | 12/2009 | Altendort |
| 7,645,050 B2 * | 1/2010 | Wilt ............... G02B 6/0008 362/103 |
| D636,104 S | 4/2011 | Chang |
| 7,918,578 B2 | 4/2011 | Spartano et al. |
| 7,942,554 B2 | 5/2011 | Alessio |
| 7,990,612 B2 | 8/2011 | Puga et al. |
| 8,047,684 B2 | 11/2011 | Chang |
| 8,144,263 B2 | 3/2012 | Hall, Jr. et al. |
| 8,218,233 B2 | 7/2012 | Uno et al. |
| D682,450 S | 5/2013 | Chang |
| 8,662,709 B2 | 3/2014 | Chang |
| 8,684,561 B2 | 4/2014 | Quadri et al. |
| 2006/0039134 A1 * | 2/2006 | Klootz ............... F21V 13/04 362/105 |
| 2007/0217198 A1 | 9/2007 | Alessi |
| 2008/0019011 A1 | 1/2008 | Kmeta et al. |
| 2009/0059095 A1 | 3/2009 | Hall, Jr. et al. |
| 2009/0161348 A1 | 6/2009 | Spartano et al. |
| 2011/0117471 A1 | 5/2011 | Devoe et al. |
| 2011/0122598 A1 | 5/2011 | Chang |
| 2012/0003565 A1 | 1/2012 | Son et al. |
| 2012/0019626 A1 | 1/2012 | Hou et al. |
| 2012/0032454 A1 | 2/2012 | Konchan et al. |
| 2012/0120635 A1 * | 5/2012 | Strong ............... F21V 21/084 362/105 |
| 2012/0120636 A1 * | 5/2012 | Wilt ............... F21V 21/084 362/105 |
| 2012/0176475 A1 | 7/2012 | Xu et al. |
| 2012/0320454 A1 * | 12/2012 | Chang ............... G02B 5/208 359/385 |
| 2013/0148195 A1 | 6/2013 | Achal |
| 2014/0049832 A1 | 2/2014 | Partridge et al. |
| 2014/0233238 A1 | 8/2014 | Quadri et al. |
| 2014/0247582 A1 | 9/2014 | Chang |
| 2014/0293588 A1 | 10/2014 | Chang |
| 2014/0334157 A1 * | 11/2014 | Ferguson ............... F21V 21/084 362/277 |
| 2014/0334159 A1 * | 11/2014 | Ferguson ............... A61B 90/35 362/311.02 |
| 2016/0123563 A1 * | 5/2016 | Ferguson ............... F21V 21/084 362/277 |

OTHER PUBLICATIONS

European Patent Office, Official Letter in corresponding European Patent Application No. 16201896.4 dated Apr. 23, 2018.

* cited by examiner

HEADLIGHT

CROSS-REFERENCE TO RELATED APPLICATIONS

This application claims the benefit of U.S. Provisional Patent Application Ser. No. 62/263,310 filed on Dec. 4, 2015, the disclosure of which is expressly incorporated by reference herein in its entirety.

TECHNICAL FIELD

The invention relates generally to lighting devices and, more particularly, to portable lighting devices, such as surgical headlights.

BACKGROUND

Portable lighting devices, such as lighting devices that are to be worn, are well known in the art. In many cases, a user may place a light on their head proximate their face. The light is then directed toward objects in the immediate vicinity of the user. As an example, these types of headlights may be used in surgical procedures. Medical and dental professionals often use surgical headlights to provide additional illumination of a surgical site on a patient. Surgical headlights may be attached to glasses or loupes to be worn by the clinician.

Existing headlights can be deficient in one or more aspects. For one, they may exhibit poor light uniformity and/or unacceptable color separation at the edge of the light beam. In addition, surgical headlights may be too heavy or awkward and are therefore uncomfortable. As such, clinicians consider size, weight, and ease of adjustment when selecting a headlight for use in surgical procedures.

To address some of these problems, U.S. Pat. No. 8,047,684 seeks to provide a more uniform light beam by positioning a singlet lens between a light-emitting diode (LED) and a doublet lens. This arrangement however has a drawback and does not address many of the clinicians' selection criteria. For example, the positioning of the doublet lens at the distal opening of the housing results in the doublet lens having a relatively large diameter, and thus the doublet lens is relatively heavy. During lengthy surgical procedures, the clinician may experience head and neck discomfort and/or pain because of the relatively heavy doublet lens.

Therefore, a need exists for a headlight which provides a more uniform light beam, and which is both lightweight and comfortable.

SUMMARY

In one embodiment, a headlight of the type worn by medical and dental professionals includes a housing having an opening therein. A light source is positioned in the housing to output light through the opening. A singlet lens is mounted in the housing proximate the opening, and a doublet lens is disposed between the light source and the singlet lens. The light source may be a light emitting diode.

The doublet lens may be achromatic. In addition or alternatively, the double lens may include first and second simple lenses. In one embodiment, a diameter of the doublet lens may be smaller than a diameter of the opening.

In one embodiment, the singlet lens may have a diameter of between about 10 mm and about 14 mm. For example, the singlet lens may have a diameter of about 10 mm. In addition or alternatively, the singlet lens may have a thickness of between about 1 mm and about 3 mm. For example, the singlet lens may have a thickness of about 2 mm.

In one embodiment, the doublet lens may have a diameter of between about 3 mm and about 7 mm. For example, the doublet lens may have a diameter of about 5 mm. In addition or alternatively, the doublet lens may have a thickness of between about 2 mm and about 4 mm. For example, the doublet lens may have a thickness of about 3 mm.

In one embodiment, the opening may have a diameter of between about 9 mm and about 14 mm.

In one embodiment, the doublet lens may be positioned proximate the light source. In addition or alternatively, the doublet lens may be positioned distally from the opening.

In one embodiment, the housing may be configured for attachment to at least one of glasses or loupes. In addition or alternatively, the light source, singlet lens, and doublet lens may be configured such that light projected from the light source through the doublet lens and singlet lens provides uniform surface illumination.

BRIEF DESCRIPTION OF THE DRAWINGS

The accompanying drawings, which are incorporated in and constitute a part of this specification, illustrate embodiments of the invention and, together with the detailed description given below, serve to explain the invention.

DETAILED DESCRIPTION

Figure 1:
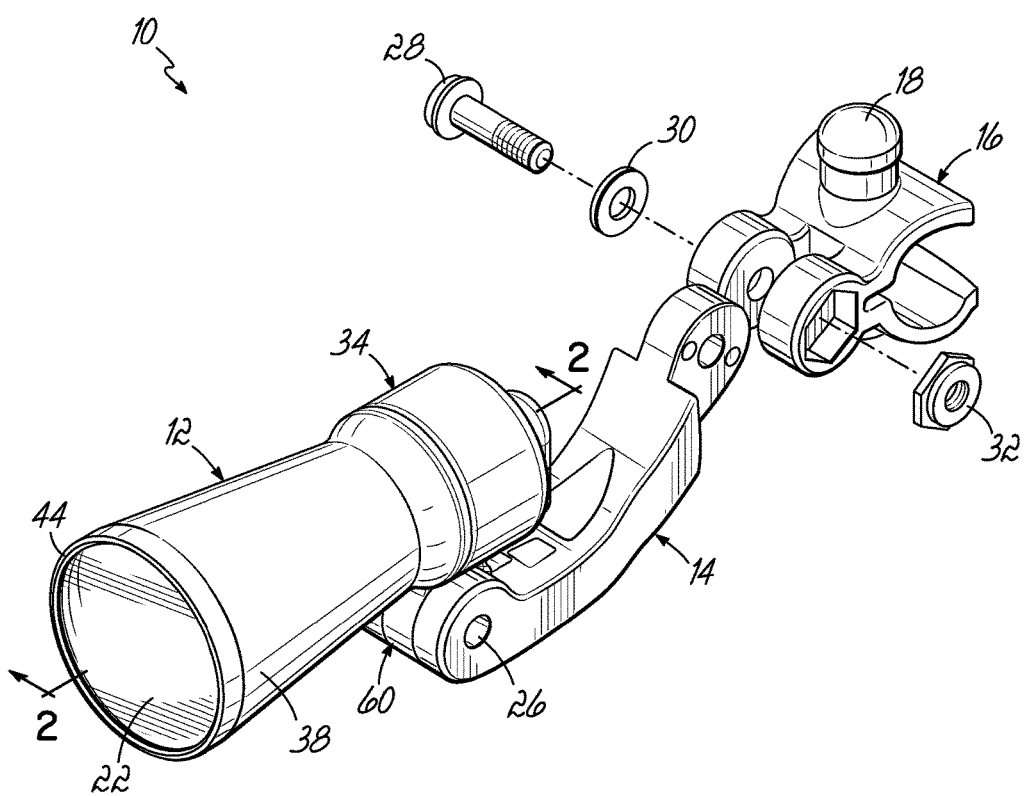
FIG. 1 is a perspective view of a headlight assembly in accordance with one embodiment of the present invention.
Figure 2:
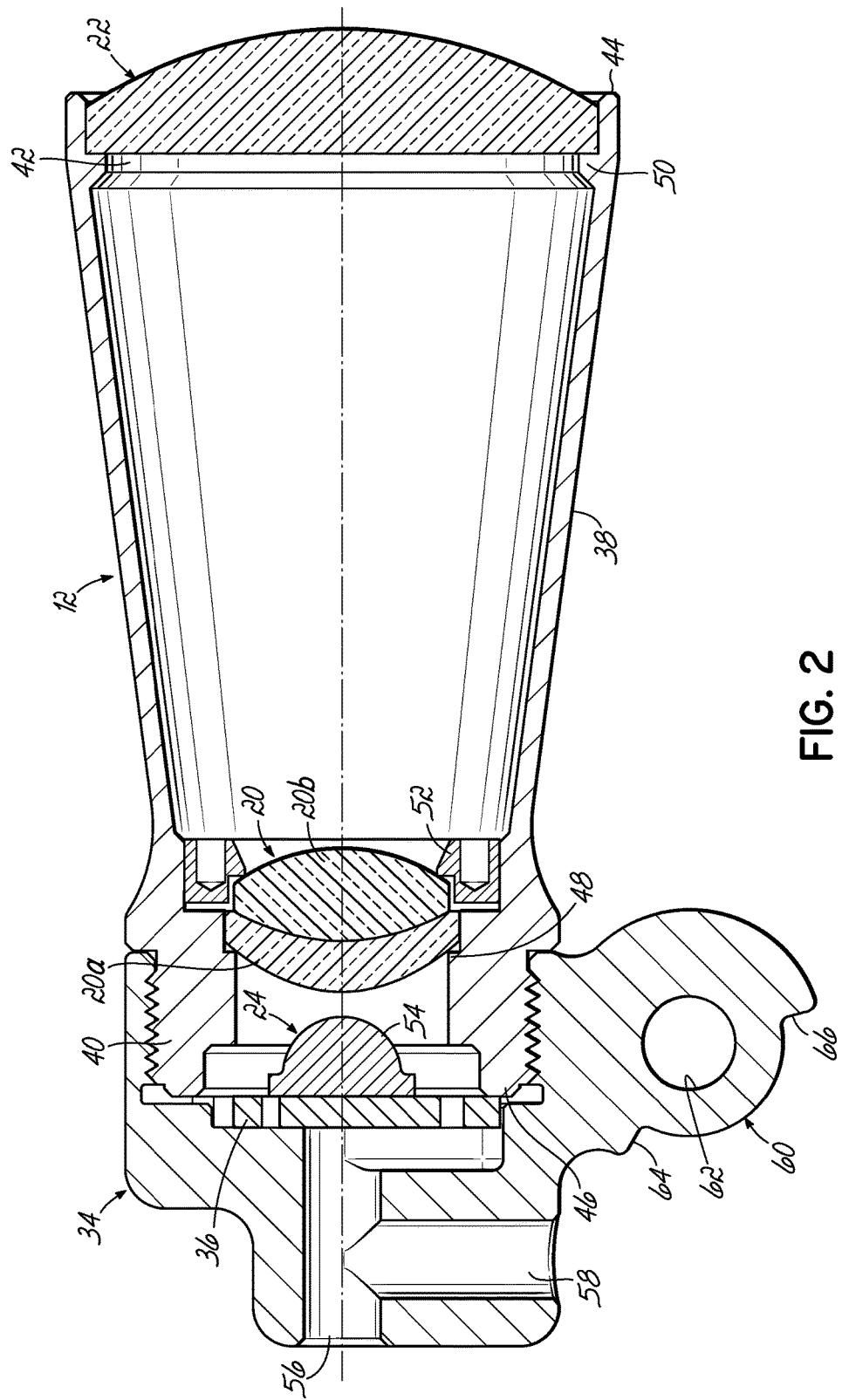
FIG. 2 is a cross-sectional view of the housing shown in FIG. 1, taken along line 2-2.

With reference to FIGS. 1 and 2, in one embodiment, a headlight assembly 10 may include a housing 12, a yoke 14, and a through-the-lens (TTL) clip 16. The TTL clip 16 may be configured for attachment to a user's glasses or loupes (not shown). For example, the TTL clip 16 may be positioned around a portion of a pair of glasses, and the thumb screw 18 may be tightened to secure the assembly 10 to the glasses. As is described below with reference to FIG. 2, multiple lenses 20, 22 and a light source 24 are arranged within the housing 12. When energized, light from the light source 24 is projected through each lens 20, 22 and out of the housing 12. Advantageously, the light beam passes through the lenses 20 and 22 to provide uniform surface illumination while the arrangement of the lenses 20, 22 in the housing 12 reduces weight, increasing user comfort.

To these and other ends, with continued reference to FIGS. 1 and 2, the housing 12, which may be constructed of aluminum, may be pivotally attached to the yoke 14. In the embodiment shown, the housing 12 is attached to a second housing 34, and the second housing 34 is pivotally attached to the yoke 14, such as by a pin 26. The yoke 14 may, in turn, be pivotally attached to the TTL clip 16, such as by a screw 28, lock washer 30, and hex nut 32.

With reference to FIG. 2, in one embodiment, the housing 12 may be threadably attached to the second housing 34 (FIG. 2), which may also be constructed of aluminum. As shown, the second housing 34 may include a fastening portion 60 including an eyelet 62 for receiving the pin 26. The fastening portion 60 may further include first and second tabs 64, 66, which may engage with corresponding features of the yoke 14 in order to provide first and second positive stops to pivotal movement of the second housing 34 relative to the yoke 14, thereby limiting the pivoting range of the second housing 34 (and consequently the housing 12) relative to the yoke 14. The second housing 34 may be proximate the light source 24 and so operate as a heat sink to dissipate heat therefrom.

The housing 12 may have a generally elongated tubular body portion 38 that extends from a base portion 40. The body portion 38 may have a generally circular cylindrical configuration that defines an opening 42 proximate one end 44 of the housing 12. The body portion 38 may join or be formed integrally with the base portion 40. The base portion 40 may be threadably attached to the second housing 34. The light source 24 is positioned within the envelope formed by the housing 12 and the second housing 34 to oppose the opening 42 proximate the other end 46 of the housing 12.

As shown, in one embodiment, the body portion 38 may include tabs 48, 50 that extend radially inward on the interior surface of the housing 12. The tabs 48, 50 may be configured to receive lenses 20, 22, respectively, in fixed position relative to one another. For example, the lenses 20, 22 may be pressed against the tabs 48, 50, and may optionally be adhered thereto. In addition, or alternatively, the body portion 38 may include a threaded retaining ring or insert 52 for receiving the lens 20 in a fixed position, such as, for example, by sandwiching the lens 20 in position against tab 48. The insert 52 is secured to the housing 12 to hold the lens 20 in position.

As shown, the light source 24 may be positioned at one end 46 of the housing 12 with the lens 20 between the lens 22 and the light source 24. In the exemplary embodiment, the lens 20 may be a doublet lens and the lens 22 may be a singlet lens. In the exemplary embodiment, the light source 24 is a light emitting diode (LED). When energized, light from the LED 24 is projected through each lens 20, 22 and out of the opening 42 of the housing 12. The LED 24 may include an integral lens 54, which may be spherical and be attached to a circuit board 36. The LED 24 may be electrically connected to a battery pack or other remote power source via a power connector (not shown). By way of example, a 0.7 mm DC power connector (not shown) may be electrically coupled to the circuit board 36. In addition, or alternatively, a battery pack and power cable sold under the trademark Orascoptic may be used. As shown, first and second passageways 56, 58 may extend through the second housing 34 and may facilitate coupling of a power cable (not shown) to the circuit board 36 and a remote power source. In the embodiment shown, the first and second passageways 56, 58 are configured to direct a power cable over, along, or through the yoke 14, in order to prevent the power cable from interfering with the clinician's line of sight or freedom of movement. More specifically, the first passageway 56 may house a portion of the power cable, and the second passageway 58 may receive a set screw for engaging a jacket of the power cable in order to provide strain relief. However, other configurations of the first and second passageways 56, 58 may be used depending on the particular application. In one embodiment, only a single passageway may be included in the second housing 34.

In one embodiment, the singlet lens 22 may be positioned at or near the distal opening 42, and may have a diameter of between about 10 mm and about 14 mm. For example, the singlet lens 22 may have a diameter of about 10 mm. The singlet lens 22 may have a thickness of between about 1 mm and about 3 mm. For example, the singlet lens 22 may have a thickness of about 2 mm.

In one embodiment, the doublet lens 20 may be achromatic, and may comprise first and second simple lenses 20a, 20b. As shown, the doublet lens 20 is positioned between the LED 24 and the singlet lens 22. In one embodiment, the doublet lens 20 may have a diameter of between about 3 mm and about 7 mm. For example, the doublet lens 20 may have a diameter of about 5 mm. The doublet lens 20 may have a thickness of between about 2 mm and about 4 mm. For example, the doublet lens 20 may have a thickness of about 3 mm.

The lenses 20, 22 and this arrangement of lenses 20, 22 relative to the LED 24 may produce a substantially uniform light beam and a substantially round, homogenous light spot at the target. Moreover, by positioning the doublet lens 20 near the LED 24, the doublet lens 20 may have a relatively small diameter, such as by comparison to the diameter of the opening 42, for example. Thus, the doublet lens 20 may be constructed of a relatively small amount of glass, and therefore be relatively lightweight, at least by comparison to a hypothetical doublet lens of similar configuration positioned at the opening 42.

The diameter of the housing 12 at the distal opening 42 may be relatively small compared to other headlights, wherein a doublet lens is typically positioned farther away from the light source (e.g. at or near an opening distal the light source). As a consequence, the diameter of the housing 12 at the distal opening 42 may be smaller relative to other headlights. By way of example and not limitation, the diameter of the housing 12 at the distal opening 42 may be from about 9 mm to about 14 mm, while the diameters of housings of other comparable headlights at their distal openings are typically from about 15 mm to about 17 mm, which may represent an approximately 10% decrease in diameter of the housing 12 at the distal opening 42 compared to other headlights. Thus, by positioning the doublet lens 20 within the housing 12 at a position away from the opening 42 and near the LED 24, the diameter of the doublet lens 20 may be minimized, reducing the overall weight of the housing 12. As described above, the headlight assembly 10 may reduce fatigue and so improve comfort by utilizing lightweight components and, more particularly, a doublet lens 20 having a relatively small diameter.

While the present invention has been illustrated by a description of various preferred embodiments and while these embodiments have been described in some detail, it is not the intention of the inventor to restrict or in any way limit the scope of the appended claims to such detail. Additional advantages and modifications will readily appear to those skilled in the art. The various features of the invention may be used alone or in any combination depending on the needs and preferences of the user.

What is claimed is:

1. A headlight of the type worn by medical and dental professionals, comprising:
    a housing having an opening therein;
    a light source positioned in the housing to output light through the opening, wherein the light source is a light emitting diode (LED);
    a singlet lens mounted in the housing proximate the opening; and
    an achromatic doublet lens including a meniscus lens in direct physical contact with a bi-convex lens disposed between the light source and the singlet lens, wherein the doublet lens and the singlet lens are arranged along a common axis, and wherein a diameter of the doublet lens is smaller than a diameter of the singlet lens.

2. The headlight of claim 1, wherein the doublet lens has a diameter and the opening has a diameter, and wherein the diameter of the doublet lens is smaller than the diameter of the opening.

3. The headlight of claim 1, wherein the singlet lens has a diameter of between about 10 mm and about 14 mm.

4. The headlight of claim 3, wherein the singlet lens has a diameter of about 10 mm.

5. The headlight of claim 1, wherein the singlet lens has a thickness of between about 1 mm and about 3 mm.

6. The headlight of claim 5, wherein the singlet lens has a thickness of about 2 mm.

7. The headlight of claim 1, wherein the doublet lens has a diameter of between about 3 mm and about 7 mm.

8. The headlight of claim 7, wherein the doublet lens has a diameter of about 5 mm.

9. The headlight of claim 1, wherein the doublet lens has a thickness of between about 2 mm and about 4 mm.

10. The headlight of claim 8, wherein the doublet lens has a thickness of about 3 mm.

11. The headlight of claim 1, wherein the opening has a diameter of between about 9 mm and about 14 mm.

12. The headlight of claim 1, wherein the doublet lens is positioned proximate the light source.

13. The headlight of claim 1, wherein the doublet lens is positioned distally from the opening.

14. The headlight of claim 1, wherein the housing is configured for attachment to at least one of glasses or loupes.

15. The headlight of claim 1, wherein the light source, singlet lens, and doublet lens are configured such that light projected from the light source through the doublet lens and singlet lens provides uniform surface illumination.

16. The headlight of claim 1, wherein the LED is attached to a circuit board positioned within the housing.

17. The headlight of claim 1, further comprising a through-the-lens (TTL) clip configured for attachment to at least one of glasses or loupes.

18. The headlight of claim 17, wherein the housing is pivotably coupled to the TTL clip.

19. The headlight of claim 1, further comprising an insert secured to the housing to hold the doublet lens in position.

20. The headlight of claim 1, further comprising a second housing threadably coupled to the housing.

21. The headlight of claim 20, further comprising a yoke, wherein the second housing includes a fastening portion including an eyelet for receiving a pin for pivotally attaching the second housing to the yoke.

22. The headlight of claim 21, wherein the fastening portion further includes first and second tabs configured to engage with the yoke to provide first and second positive stops to pivotal movement of the second housing relative to the yoke.

23. The headlight of claim 20, wherein the second housing includes first and second passageways, and wherein the first passageway is configured to house a portion of a power cable for supplying power to the LED and the second passageway is configured to receive a set screw for engaging the power cable.

* * * * *